US011731746B2

(12) United States Patent
Fujimoto

(10) Patent No.: US 11,731,746 B2
(45) Date of Patent: Aug. 22, 2023

(54) SWIMMING MASK

(71) Applicant: TABATA CO., LTD., Tokyo (JP)

(72) Inventor: Takashi Fujimoto, Tokyo (JP)

(73) Assignee: TABATA CO., LTD., Tokyo (JP)

( * ) Notice: Subject to any disclaimer, the term of this patent is extended or adjusted under 35 U.S.C. 154(b) by 33 days.

(21) Appl. No.: 17/483,813

(22) Filed: Sep. 24, 2021

(65) Prior Publication Data

US 2022/0097810 A1 Mar. 31, 2022

(30) Foreign Application Priority Data

Sep. 25, 2020 (JP) .................. 2020-161475

(51) Int. Cl.
 *B63C 11/12* (2006.01)
 *A63B 33/00* (2006.01)
 *A61F 9/02* (2006.01)

(52) U.S. Cl.
 CPC .............. *B63C 11/12* (2013.01); *A61F 9/026* (2013.01); *A63B 33/002* (2013.01); *B63C 2011/128* (2013.01)

(58) Field of Classification Search
 CPC ......... B63C 11/12; A63B 33/002; A61F 9/026
 See application file for complete search history.

(56) References Cited

U.S. PATENT DOCUMENTS

| 7,451,498 | B2 * | 11/2008 | Kuroda | .................. B63C 11/12 2/9 |
| 9,156,532 | B2 * | 10/2015 | Shiue | ..................... B63C 11/12 |
| 9,663,204 | B2 * | 5/2017 | Kuroda | .................. B63C 11/12 |
| 2020/0276364 | A1 * | 9/2020 | Gandola | ........... A61M 16/0622 |
| 2022/0017190 | A1 * | 1/2022 | Godoy | .................... B63C 11/12 |

FOREIGN PATENT DOCUMENTS

| FR | 920668 A | * | 1/1946 |
| GB | 932258 A | * | 3/1961 |
| JP | 2004136057 A | | 5/2004 |

* cited by examiner

*Primary Examiner* — F Griffin Hall
(74) *Attorney, Agent, or Firm* — Hauptman Ham, LLP

(57) ABSTRACT

In a swimming mask, a skirt includes a circumferential wall in an annular shape extending rearward from a lens frame, and a seal portion disposed behind the circumferential wall to be brought into contact with a face of a wearer. The skirt also includes a high stiffness annular region disposed rearward apart from the lens frame, extending in both side regions and an upper region of a mask body, and having higher stiffness than stiffness of other part of the skirt.

5 Claims, 11 Drawing Sheets

SWIMMING MASK

RELATED APPLICATIONS

The present application claims priority based on Japanese Patent Application No. 2020-161475, filed Sep. 25, 2020, the disclosure of which is hereby incorporated by reference herein in its entirety.

BACKGROUND OF THE INVENTION

The present invention relates to a swimming mask including a flexible skirt extending rearward from a lens frame.

The swimming mask including the flexible skirt has been conventionally known. For example, JP-A-2004-136057 discloses a swimming mask including a lens frame for fixing a lens, a flexible skirt extending rearward from the lens frame to cover a face of a wearer, and a head strap connected to both ends of the skirt.

SUMMARY OF THE INVENTION

When a swimming mask disclosed in JP-A-2004-136057 is worn, a strap is pulled rearward to bring a flexible annular skirt into contact with a face. Compared with a case of pressing a member made of a rigid material against a face, an excellent wearing feeling can be exerted and flow of water into the swimming mask can be prevented under water.

However, when the swimming mask is worn, the whole flexible skirt is pulled rearward by the head strap to be brought into contact with a head. As a result, for wearers with heads having a relatively small width such as Westerners, both side portions of the skirt make relatively loose contact with the face, which may cause a shift in position. On the other hand, for wearers with faces having a relatively wide width such as Asians including the Japanese, both the side portions of the skirt make relatively strong contact with the face, which may cause uncomfortable feeling to the wearers.

Furthermore, when the whole swimming mask is moved rearward, pressure in the mask already in negative is further reduced, which may give the wearers a tightening feeling or leave an oppression trace on the face after removal of the swimming mask.

Furthermore, a seal portion in the skirt in direct contact with the face is pressed against the face as it is, and does not change the shape to conform to the shape of the face of the wearer. Accordingly, only an outer circumferential edge portion of the seal portion is strongly pressed against the face, which may impair a fit property.

An object of the present invention is to improve the conventional swimming mask to provide a swimming mask including a skirt that can exert an excellent sealing property for heads of various sizes.

In order to achieve the object, first and second inventions of the present application are directed to a swimming mask having a front-back direction and including a mask body having a lens frame and a skirt extending rearward from the lens frame.

In the swimming mask according to the first invention of the present application, the skirt includes a circumferential wall in an annular shape extending rearward from the lens frame, and a seal portion disposed behind the circumferential wall to be brought into contact with a face of a wearer. The skirt also includes a high stiffness annular region disposed rearward apart from the lens frame, extending in both side regions and an upper region of the mask body, and having stiffness higher than stiffness of other part of the skirt.

In the swimming mask according to the second invention of the present application, the skirt includes the circumferential wall in an annular shape extending rearward from the lens frame and the seal portion disposed behind the circumferential wall to be brought into contact with a face of a wearer. The seal portion includes an outward extending portion extending outward from a rear end edge of the circumferential wall, and the circumferential wall includes a low stiffness annular region extending annularly along a base end of the outward extending portion.

Embodiments described below relate to the swimming mask according to a first embodiment shown in FIGS. 1 to 7, and include both optional and preferable features as well as essential features of the present invention.

(1) The swimming mask further includes a head strap configured to be connected to the mask body, and a connecting unit for connecting the head strap to the mask body is disposed in the high stiffness annular region.

(2) The high stiffness annular region includes a front portion, and a rear portion disposed behind the front portion and having a thickness dimension larger than a thickness dimension of the front portion.

In the swimming mask according to the present invention, since the skirt includes the high stiffness annular region, the swimming mask locally fits the head of the wearer, and the seal portion can evenly apply pressure to the face by both side regions of the mask body. As a result, the swimming mask can exert an excellent sealing property for various shapes of faces of wearers.

BRIEF DESCRIPTION OF DRAWINGS

The drawings illustrate specific embodiments of a swimming mask according to the present invention including optional and preferred embodiments as well as essential features of the invention.

DESCRIPTION OF EMBODIMENTS

Figure 1:
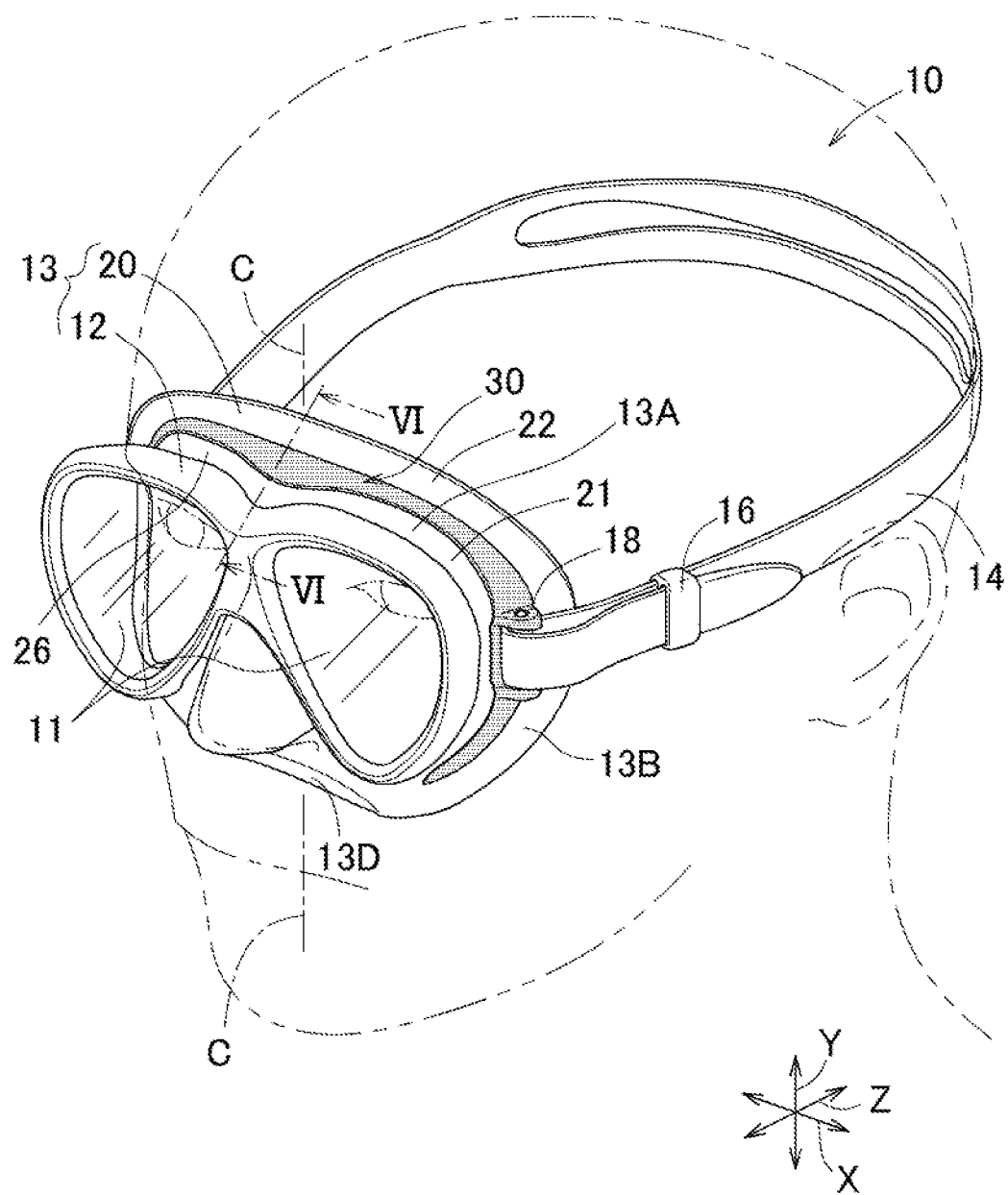
FIG. 1 is a perspective view of a swimming mask according to a first embodiment of the present invention.

Referring to the accompanying drawings, details of an swimming mask 10 according to the present invention are described as follows. In FIG. 1, a front-back direction of the swimming mask 10 is represented by Z, a vertical direction by Y, and a transverse direction by X. A line C-C represents an imaginary center line bisecting a dimension of the swimming mask 10 in the transverse direction. The swimming mask 10 is symmetrical with respect to the line C-C. Inward (inside) in the transverse direction X means a direction toward the center line C-C, and outward (outside) in the transverse direction X means a direction opposite to the inward direction.

As shown in FIGS. 1 to 5, the swimming mask 10 includes a mask body 13 and a head strap 14. The mask body 13 includes a lens frame 12 in which a pair of lenses 11 are set, and a flexible skirt 20 extending rearward from the lens frame 12. The head strap 14 is configured to be connected to both sides of the mask body 13. The mask body 13 includes an upper region 13A extending in the transverse direction X, both side regions 13B and 13C opposed to each other in the transverse direction X, and a lower region 13D extending in the transverse direction below a nose cover.

In an example shown in the drawings, the pair of lenses 11 are formed of a pair of transparent plates; however, one continuous transparent plate may be used. The head strap 14 is wound around a connector, e.g., connecting units 18 disposed on both sides of the mask body 13, and both end portions of the head strap 14 are held by figure eight rings 16. However, a length may be adjustable by a buckle (not shown).

The connecting units 18 are disposed on both sides of the skirt 20, not of the lens frame, in the mask body 13. This prevents the lens frame 12 from moving rearward toward a face when the swimming mask is worn, and thus prevents pressure in the swimming mask 10 from becoming more negative than required.

The lens frame 12 is made of a rigid plastic material. On the other hand, the skirt 20 and the head strap 14 are made of a soft material such as a natural or synthetic rubber, a silicone resin, or a thermoplastic synthetic resin.

The skirt 20 includes a circumferential wall 21 in an annular shape disposed behind the lens frame 12 in the upper region 13A and both side regions 13B and 13C of the mask body 13, and a seal portion (a face contact portion) 22 in an annular and flange shape disposed behind the circumferential wall 21. The seal portion 22 is a portion to be brought into direct contact with the face of the wearer, and extends outward from the circumferential wall 21 in a radial direction.

Figure 2:
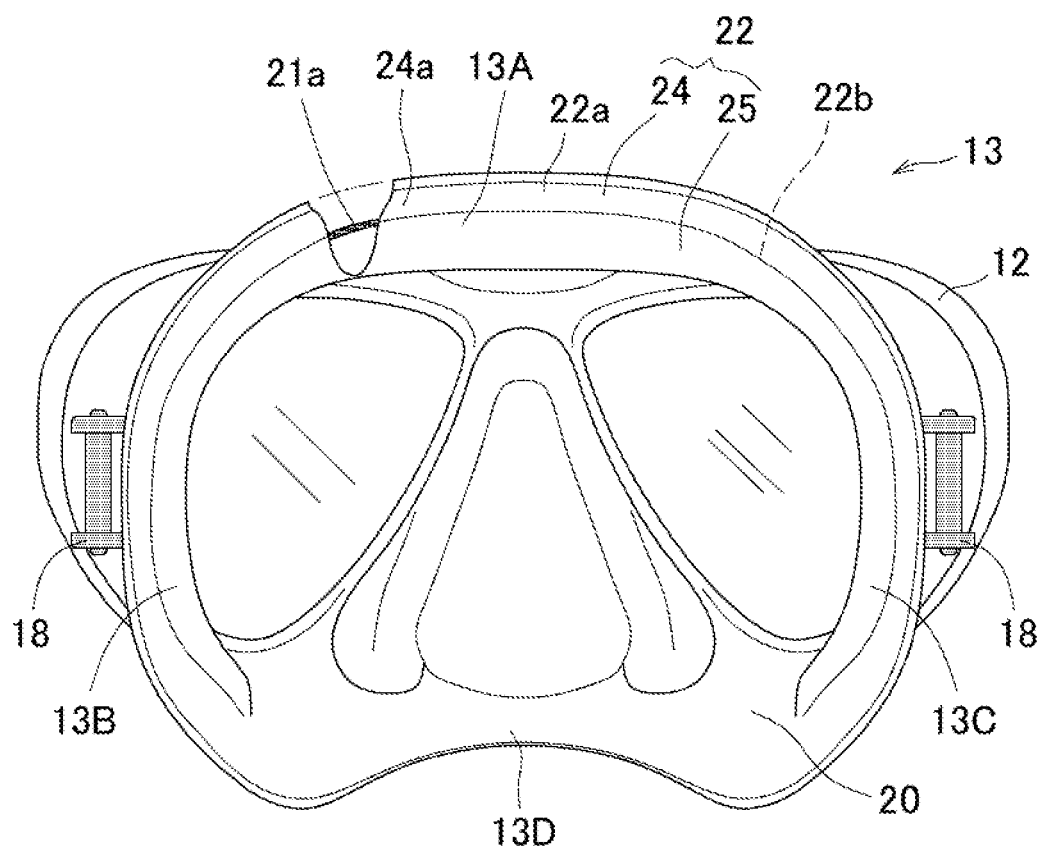
FIG. 2 is a view of a mask body seen from behind.

Referring to FIG. 2, the seal portion 22 includes an inner surface 22a to be brought into contact with an outer surface of the wearer, an outer surface 22b, an outward extending portion 24 extending outward in the radial direction from a rear circumferential edge 21a of the circumferential wall 21, and an inward extending portion 25 extending inward in the radial direction from the rear circumferential edge of the circumferential wall 21.

The circumferential wall 21 of the skirt 20 includes a front portion 26 adjacent to the lens frame 12, and a high stiffness annular region (a fitting ring) 30 disposed behind and adjacently to the front portion 26.

The high stiffness annular region 30 is a region having higher stiffness than stiffness of a remaining region (a region other than the high stiffness annular region 30) of the circumferential wall 21 of the skirt 20. In the example shown in the drawings, the high stiffness annular region 30 is formed thicker than the remaining region of the circumferential wall 21 so as to have relatively high stiffness. However, the high stiffness annular region 30 may be made of a material that differs from the material forming the remaining region and has high stiffness, and have the same thickness as a thickness of the remaining region, as long as the high stiffness annular region 30 has relatively high stiffness.

Figure 3:
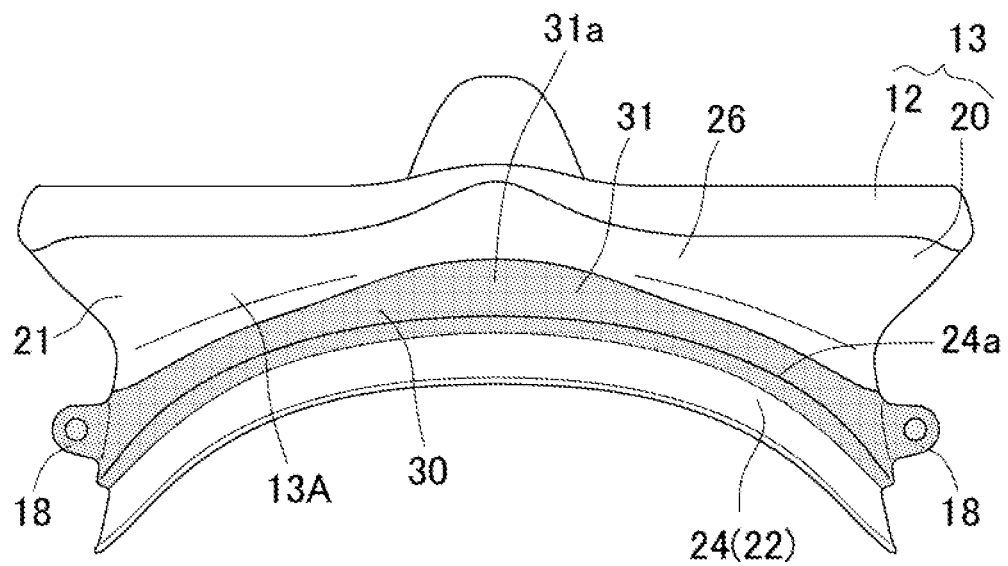
FIG. 3 is a view of the mask body seen from above.
Figure 3:
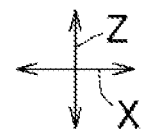
Figure 4:
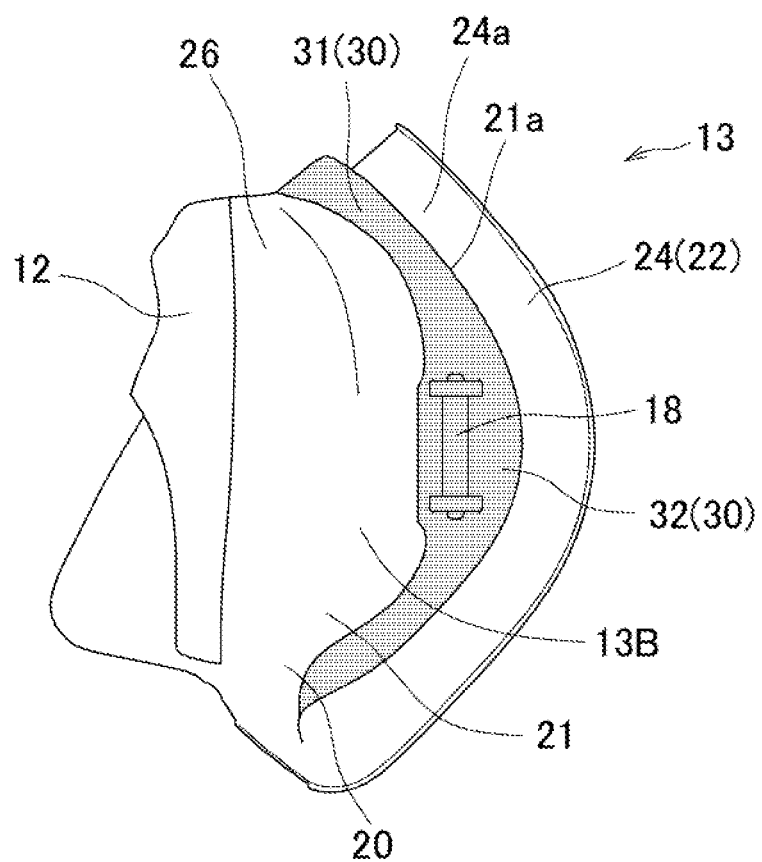
FIG. 4 is a side view of the mask body.

Referring to FIGS. 3 and 4, the high stiffness annular region 30 extends from the side region 13B on one side of the mask body 13 to the side region 13C on the other side through the upper region 13A, and includes a transverse portion 31 in the upper region 13A and both end portions 32 and 33 in both the side regions 13B and 13C, respectively. The transverse portion 31 has a wave shape protruding forward at its center portion 31a. A rear end edge of the high stiffness annular region 30 overlaps the rear end edge of the circumferential wall 21.

Figure 5:
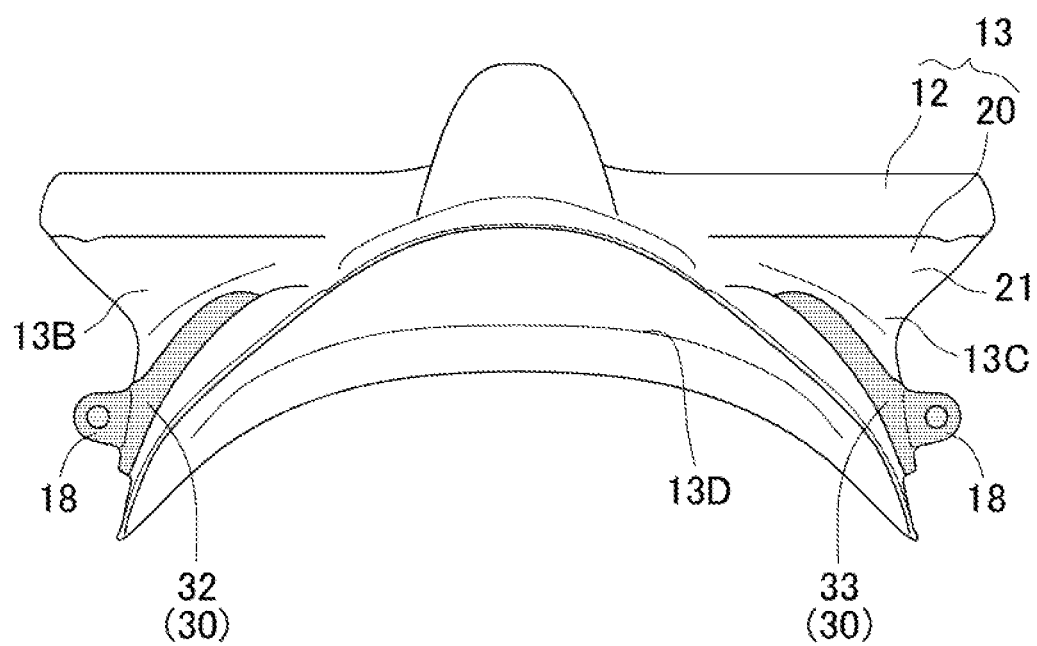
FIG. 5 is a view of the mask body seen from below.
Figure 5:
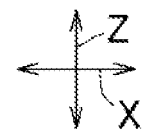

Referring to FIG. 5, both the end portions 32 and 33 of the high stiffness annular region 30 do not extend in the lower region 13D of the mask body 13. Thus, the high stiffness annular region 30 does not restrict a movement of a mouth of the wearer.

Figure 7:
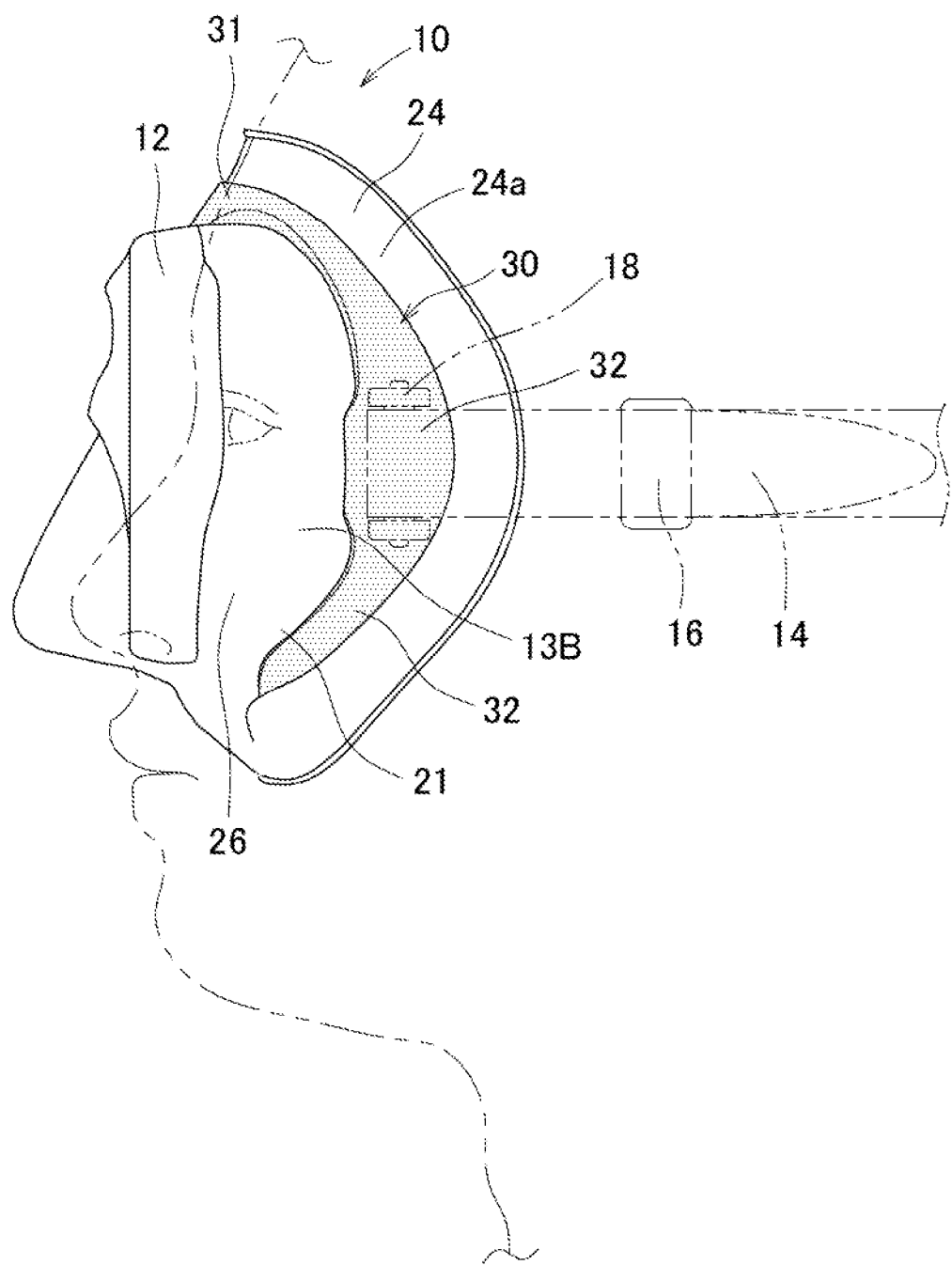
FIG. 7 is a cross-sectional view taken along line VII-VII in FIG. 1.

Referring to FIG. 7, when the swimming mask is worn, the high stiffness annular region 30 fits the face of the wearer. When the whole flexible skirt 20 is brought into contact with the wearer, the fit property may be impaired or a feeling of pressure may be given depending on a width of the head of the wearer, in a usual condition. According to the present embodiment, the high stiffness annular region 30 having higher stiffness than the stiffness of the remaining region of the skirt 20 fits the face; especially, both the end portions 32 and 33 of the high stiffness annular region 30 stably fit both sides of the face. Thus, the pressure by the seal portion 22 is evenly applied to the face through both the side regions 13B and 13C of the mask body 13.

As a result, even when the wearer has a narrow sharp face and a head relatively small in width, no shift in position is caused. Furthermore, even when the wearer has a wide flat face and a head relatively large in width, not the whole of the skirt 20 strongly fits the face, but only the high stiffness annular region 30, which is circularly extending, locally and tightly fits the face. This can prevent giving the feeling of pressure, and give a wearing feeling like being wrapped by the skirt 20.

The connecting units 18 for the head strap 14 are disposed in the high stiffness annular region 30. Thus, rearward tensile force caused by the head strap 14 applies not to the whole skirt 20, but only to the high stiffness annular region 30. This prevents the whole mask body 13 from moving rearward. As a result, the pressure in the swimming mask 10 does not become more negative than required to give the wearer tightening feeling. In addition, compared with a case where the connecting units 18 are disposed in the remaining region of the circumferential wall 21, tensile strength of the connecting units 18 can be enhanced.

Furthermore, the front portion 26 of the circumferential wall 21 is disposed between the lens frame 12 and the high stiffness annular region 30. The front portion 26 has more flexibility and lower stiffness than those of the high rigid lens frame 12 made of a rigid plastic material and the high stiffness annular region 30. As a result, when the swimming mask is worn, the front portion 26 absorbs force in the front-back direction causing the shift in position of the lens frame 12 and/or high stiffness annular region 30, so that the skirt 20 can maintain a fit state to the face.

Figure 6:
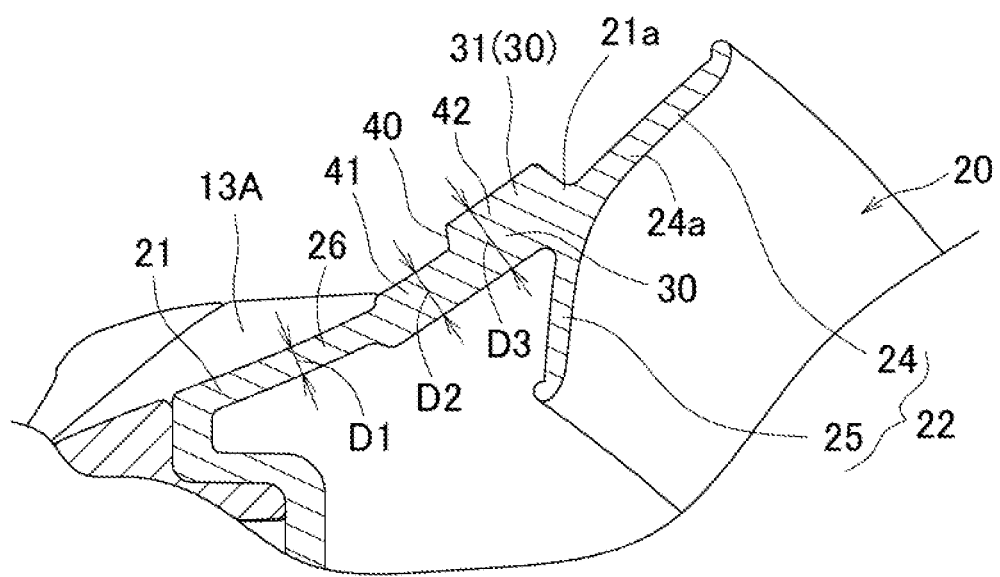
FIG. 6 is a cross-sectional view taken along line VI-VI in FIG. 1.

Referring to FIG. 6, the high stiffness annular region 30 includes a step 40 extending in a circumferential direction, a front portion 41, and a rear portion 42 that is even thicker than the front portion 41. Accordingly, since the rear portion 42 is thicker and has higher stiffness than the front portion 41 in the high stiffness annular region 30, pressure can be applied more locally and evenly to the face of the wearer.

Referring to FIG. 6, thickness dimensions of respective portions of the skirt 20 are described here. A thickness dimension D2 of the front portion 41 of the high stiffness annular region 30 is 1.5 to 3.0 times as large as a thickness dimension D1 of the remaining region other than the high stiffness annular region 30. A thickness dimension D3 of the rear portion 42 is 1.5 to 4.0 times as large as the thickness dimension D2 of the front portion 41.

Second Embodiment

Figure 8:
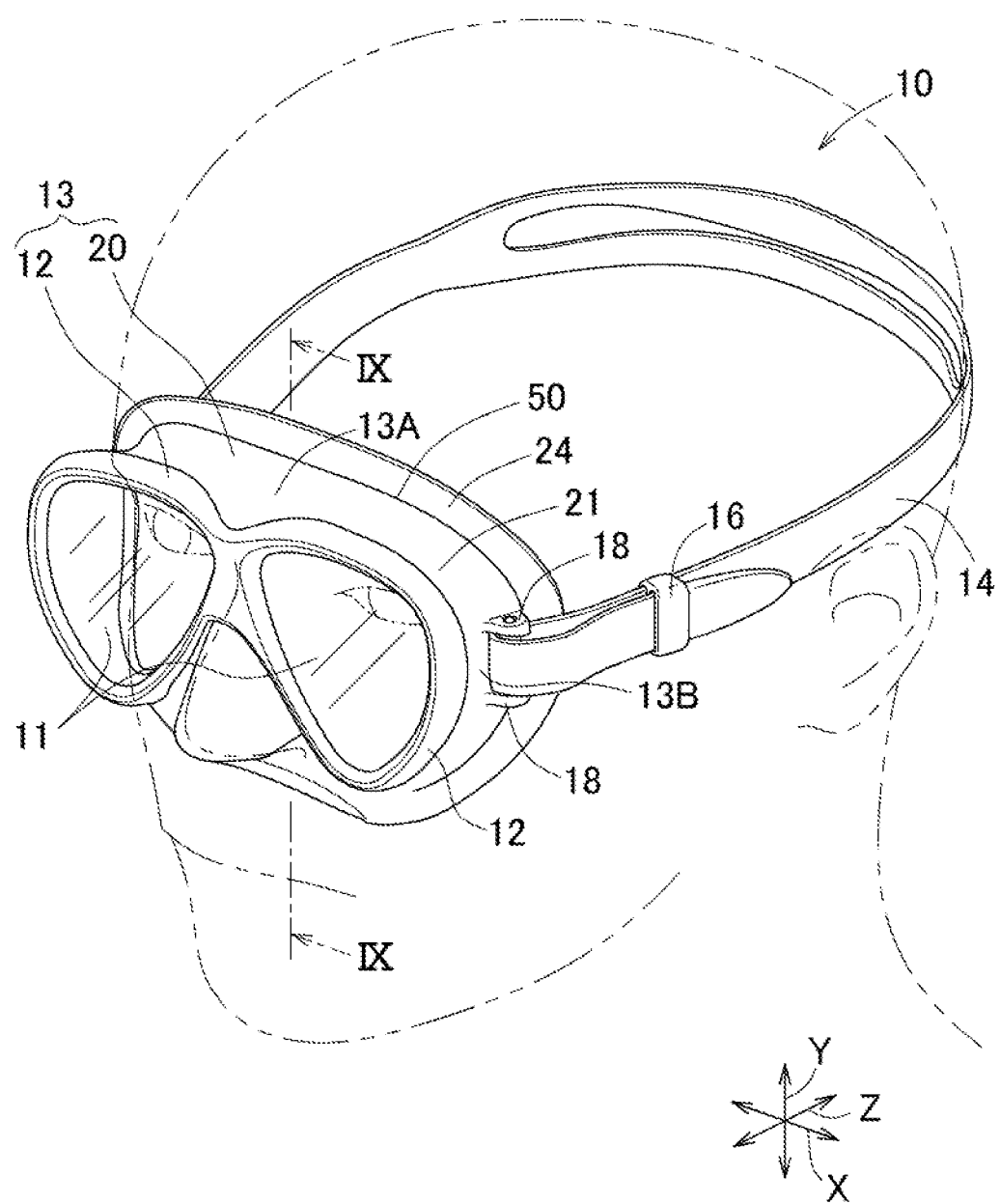
FIG. 8 is a perspective view of a swimming mask according to a second embodiment of the present invention.
Figure 9A:
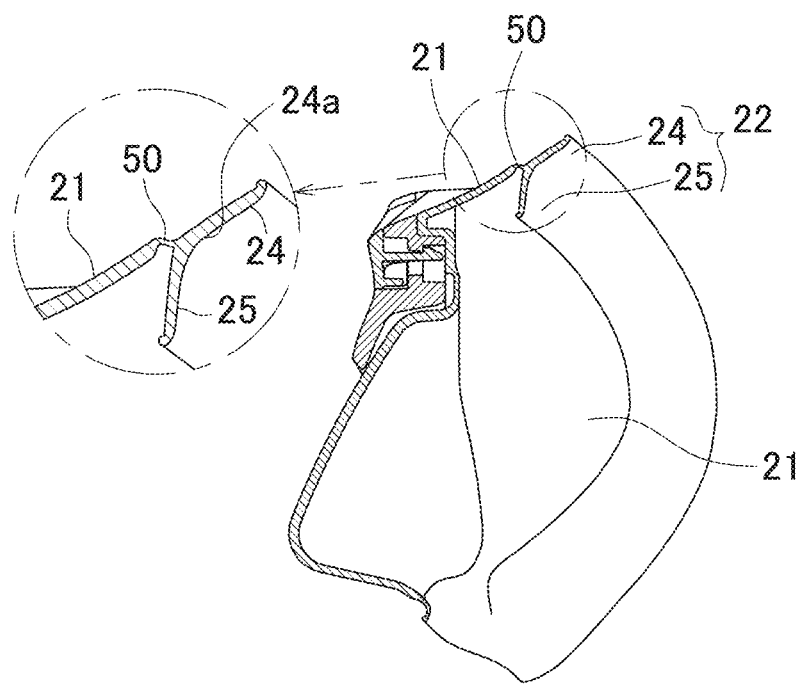
FIG. 9A is a partial cross-sectional view of a mask body when the swimming mask is not worn.
Figure 9B:
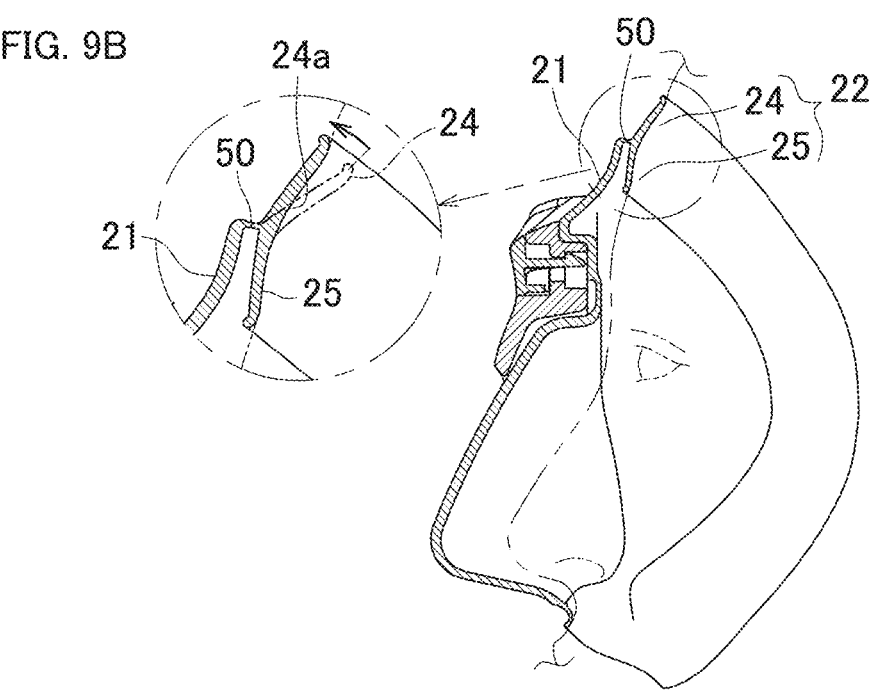
FIG. 9B is a cross-sectional view taken along the line IX-IX in FIG. 8.

Referring to FIGS. 8, 9A and 9B, the swimming mask 10 according to a second embodiment of the present invention has the same basic configuration as that of the swimming mask 10 according to the first embodiment, and only different configurations are described below.

The skirt 20 of the swimming mask 10 according to the present embodiment does not include the high stiffness annular region 30 but a low stiffness annular region (a hinge region) 50 instead. That is, the skirt 20 includes the low stiffness annular region 50 that extends in the circumferential direction along a base end 24a of the outward extending portion 24 of the seal portion 22 and has stiffness lower than stiffness of a remaining region (a region other than the low stiffness annular region 50) of the circumferential wall 21 of the skirt 20. With the low stiffness annular region 50 of the seal portion 22, the outward extending portion 24 can easily swing in the front-back direction Z via the low stiffness annular region 50.

Referring to FIG. 9A, the low stiffness annular region 50 includes a thin portion formed in the circumferential direction along the base end 24a of the outward extending portion 24 of the seal portion 22 in the circumferential wall 21. However, the low stiffness annular region 50 may be made of a material that differs from the material forming the remaining region and has low stiffness, and have the same thickness as a thickness of the remaining region, as long as the low stiffness annular region 50 has relatively low stiffness.

As for conventional swimming masks, only an outer circumferential edge of the outward extending portion of the seal portion in a cup shape is brought into contact with the face, and the whole inner surface of the outward extending portion does not easily fit the face.

Referring to FIG. 9B, when the swimming mask 10 is worn, the low stiffness annular region 50 functions as a hinge portion that raises the base end 24a of the outward extending portion 24 of the seal portion 22. Thus, when the swimming mask 10 is worn, the outward extending portion 24 is brought into contact with the face, so that the base end 24a of the outward extending portion 24 in a lying back state, as shown by an imaginary line in FIG. 9A, is put in a standing state.

As a result, since the whole inner surface of the outward extending portion 24 fits the face in a planar manner when the swimming mask 10 is worn, a higher sealing property can be exerted, compared with a case where the outward extending portion 24 in the lying back state is brought into contact with the face as it is.

In order to implement the hinge function of the low stiffness annular region 50, a thickness dimension of the low stiffness annular region 50 is preferably 0.3 to 0.7 times as large as a thickness dimension of the remaining region of the circumferential wall 21. When the thickness dimension is equal to or smaller than 0.3 times, continuous use may cause a bent mark or a crack. When the thickness dimension is over 0.7 times, the outward extending portion 24 may not be raised.

Third Embodiment

Figure 10:
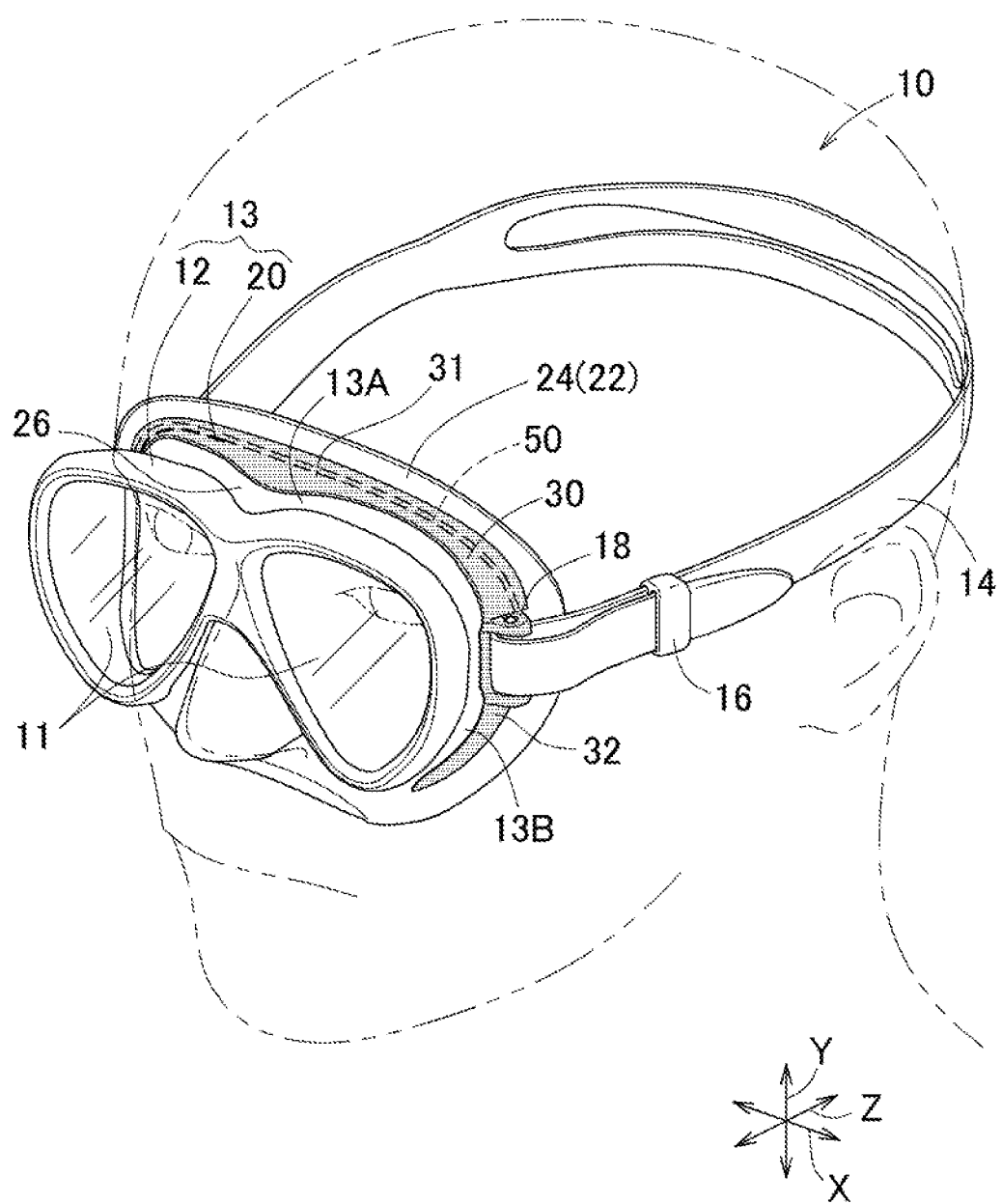
FIG. 10 is a perspective view of a swimming mask according to a third embodiment of the present invention.
Figure 11:
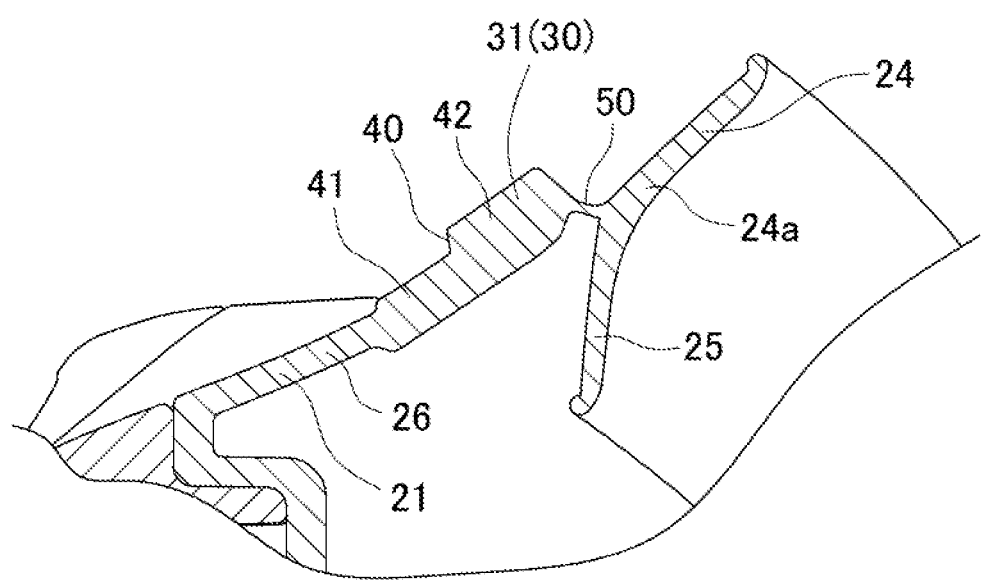
FIG. 11 is a cross-sectional view, similar to FIG. 6, of the swimming mask according to the third embodiment.

Referring to FIGS. 10 and 11, the swimming mask 10 according to a third embodiment of the present invention has the same basic configuration as that of the swimming mask 10 according to the first embodiment, and only different configurations are described below.

The skirt 20 of the swimming mask 10 according to the present embodiment includes both the high stiffness annular region 30 according to the first embodiment and the low stiffness annular region 50 according to the second embodiment. That is, the low stiffness annular region 50 is disposed along the rear circumferential edge of the high stiffness annular region 30.

Referring to FIG. 11, when the swimming mask 10 is worn, the skirt 20 locally and tightly fits the face of the wearer by the high stiffness annular region 30, so that force by the seal portion 22 toward the face is evenly applied through both the side regions 13B and 13C. Furthermore, the outward extending portion 24 of the seal portion 22 fits the face in the standing state due to the low stiffness annular region 50, so that the sealing property of the seal portion 22 can be enhanced.

That is, since the skirt 20 includes the high stiffness annular region 30 and the low stiffness annular region 50, pressure by the seal portion 22 can be evenly and widely applied, so that the seal portion 22 can exert the high sealing property with respect to the face. Furthermore, since the low stiffness annular region 50 extends along the rear circumferential edge of the high stiffness annular region 30, a difference in stiffness becomes larger than a difference in the second embodiment. As a result, the outward extending portion 24 can be more easily raised via the low stiffness annular region 50.

The swimming mask 10 including the high stiffness annular region 30 according to the first embodiment of the present invention and the swimming mask 10 including the low stiffness annular region 50 according to the second embodiment may be adapted independently as a means for enhancing the sealing property of the seal portion 22. That is, the sealing property may be enhanced by evenly applying the pressure of the outward extending portion 24 of the seal portion 22 through both the side regions 13B and 13C by the high stiffness annular region 30, or may be enhanced by raising the outward extending portion 24 via the low stiffness annular region 50 to fit the whole inner surface of the outward extending portion 24 to the face.

Furthermore, as described above, when the skirt 20 includes both the high stiffness annular region 30 and the low stiffness annular region 50, the seal portion 22 can change the shape to synchronize with the shape of the face to exert a higher sealing property, compared with a case including only one of these regions. Various known materials generally used in this kind of field can be used without limitation for constituent materials included in the swimming mask 10, unless otherwise described in this specification. Terms such as "first" or "second" used in this specification are used simply to distinguish similar elements, positions, or the like.

What is claimed is:
1. A swimming mask having a front-back direction and comprising:

a mask body including a lens frame and a skirt extending rearward from the lens frame,
wherein
the skirt includes
- a circumferential wall in an annular shape extending rearward from the lens frame and
- a seal portion disposed behind the circumferential wall and configured to be brought into contact with a face of a wearer, the skirt includes a high stiffness annular region disposed rearward apart from the lens frame, extending in both side regions and an upper region of the mask body, and having a stiffness higher than a stiffness of a remaining part of the skirt, a front portion of the circumferential wall is disposed between the lens frame and the high stiffness annular region, the front portion of the circumferential wall has more flexibility and lower stiffness than the lens frame and the high stiffness annular region, the high stiffness annular region includes:
- a front portion, and
- a rear portion disposed behind the front portion of the high stiffness annular region and having a thickness dimension larger than a thickness dimension of the front portion of the high stiffness annular region, and the thickness dimension of the front portion of the high stiffness annular region is greater than a thickness dimension of the front portion of the circumferential wall.

2. The swimming mask according to claim 1, further comprising a head strap configured to be connected to the mask body, wherein a connector configured to connect the head strap to the mask body is disposed in the high stiffness annular region.

3. A swimming mask having a front-back direction and comprising
a mask body including a lens frame and a skirt extending rearward from the lens frame,
wherein
the skirt includes
- a circumferential wall in an annular shape extending rearward from the lens frame and
- a seal portion disposed behind the circumferential wall and configured to be brought into contact with a face of a wearer, the seal portion includes an outward extending portion extending outward from a rear end edge of the circumferential wall, and the circumferential wall includes a low stiffness annular region extending annularly along a base end of the outward extending portion.

4. The swimming mask according to claim 3, wherein the low stiffness annular region of the circumferential wall has a stiffness lower than a stiffness of a remaining region of the circumferential wall.

5. The swimming mask according to claim 3, wherein the low stiffness annular region of the circumferential wall is configured to function as a hinge to raise the base end of the outward extending portion of the seal portion such that when the swimming mask is worn, the outward extending portion is brought into contact with the face of the wearer.

* * * * *